United States Patent

Lutz et al.

[11] 3,981,715
[45] Sept. 21, 1976

[54] 2,3,5-SUBSTITUTED-6-TRIFLUOROMETHYL-1,3-DIAZIN-4-ONES HERBICIDES

[75] Inventors: Albert William Lutz, Princeton; Bryant Leonidas Walworth, Pennington, both of N.J.

[73] Assignee: American Cyanamid Company, Stamford, Conn.

[22] Filed: Sept. 9, 1974

[21] Appl. No.: 504,230

Related U.S. Application Data

[60] Division of Ser. No. 237,936, March 24, 1972, Pat. No. 3,869,457, which is a continuation-in-part of Ser. No. 737,308, June 17, 1968, abandoned.

[52] U.S. Cl. .................................................. 71/92
[51] Int. Cl.$^2$............................................ A01N 9/22
[58] Field of Search ........................................... 71/92

[56] References Cited
UNITED STATES PATENTS

| | | |
|---|---|---|
| 3,235,358 | 2/1966 | Soboczenski ............................ 71/92 |
| 3,235,363 | 2/1966 | Luckenbaugh et al. ................ 71/92 |
| 3,580,913 | 5/1971 | Lutz ..................................... 71/92 X |

*Primary Examiner*—Lewis Gotts
*Assistant Examiner*—Catherine L. Mills
*Attorney, Agent, or Firm*—H. G. Jackson

[57] ABSTRACT

Herbicidal compounds are disclosed having the general formula

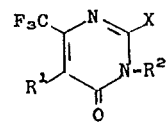

where X is hydrogen or hydroxy, $R^1$ is hydrogen or halo and $R^2$ is alkyl, cycloalkyl, phenyl, alkenyl, and substituted derivatives of the above. Compounds for which herbicidal usage is claimed may include, in addition to the compounds of formula (I), formula (I) compounds in which $R^2$ is hydrogen.

8 Claims, No Drawings

2,3,5-SUBSTITUTED-6-TRIFLUOROMETHYL-1,3-DIAZIN-4-ONES HERBICIDES

This is a division of copending application Ser. No. 237,936, filed Mar. 24, 1972 which is now U.S. Pat. No. 3,869,457 (1975) which was a continuation in part of application Ser. No. 737,308, filed June 17, 1968, now abandoned.

SUMMARY OF THE INVENTION

This invention relates to novel 2,3,5-substituted-6-trifluoromethyl-1,3-diazin-4-ones having the formula:

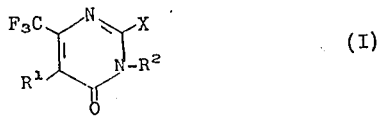

(I)

wherein:
$R^1$ is hydrogen or halo,
$R^2$ is alkyl, cycloalkyl, phenyl, alkenyl and substituted derivatives of these radicals, and
X is hydrogen or hydroxy.

The various R groupings referred to hereinabove may be more particularly identified as follows:

The term "alkyl" means straight and branched chain alkyl radicals containing from 1 to 12 carbon atoms; illustrative members include "lower alkyls" as defined above but also include other members such as pentyl, hexyl, heptyl, octyl, nonyl, decyl, undecyl, dodecyl, 2-methylhexyl, 3,3-dimethylpentyl, triisopropylmethyl, and 1-ethylpropyl.

The term "cycloalkyl" means saturated cyclic structures containing from 3 to 8 carbon atoms; illustrative members are cyclopropyl, cyclobutyl, cyclopentyl, cyclohexyl, cycloheptyl, and cyclooctyl.

The term "alkenyl" means unsaturated straight and branched hydrocarbon chains containing from 2 to 6 carbon atoms; illustrative members are allyl, 2-butenyl and 2-methylallyl.

The term "halo" means chlorine, bromine, iodine, and fluorine.

The terms "substituted alkyl", "substituted cycloalkyl", "substituted alkenyl", "substituted phenyl" mean that the basic radical may contain up to two substituents selected from the group consisting of halo, nitro, amino, lower alkyl, monohalo(lower)alkyl, polyhalo(lower)alkyl, lower alkoxy, carboxy, and carbalkoxy; illustrative substituents include 2-methoxyethyl, 3-methoxypropyl, 2-bromopropyl, 4-chlorobutyl, 2-nitrophenyl, 2-carbomethoxypropyl, 3-bromo-2-methoxypropyl, tolyl, 3,4-dichlorophenyl, p-aminophenyl, m-trifluoromethylphenyl, p-carboxyphenyl, 2,4-dichlorophenyl, and the like. When two substituents are present, they may be identical or dissimilar.

The term "carbalkoxy" is limited to the lower alkoxys as defined above; illustrative members are carbomethoxy, carboethoxy, carbopropoxy, and carbobutoxy.

Certain of the inventive compounds, i.e., those wherein X is hydroxy and/or when $R^2$ is hydrogen may exhibit tautomeric forms such as those shown by way of example below:

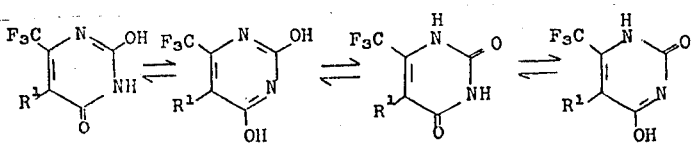

Such tautomeric structures are included within the scope of the invention as are the water soluble salts, particularly the sodium, potassium and ammonium salts, of the compounds and tautomers.

These salts are readily formed by a conventional acid-base reaction of the appropriate uracil with a base. Suitable bases include, for example, sodium or potassium hydroxide. The ammonium salts are prepared by using ammonium hydroxide or a $C_1$-$C_4$ tertiary amine, such as trimethyl or triethylamine as the base. The acid-base reactions are usually conducted in a solvent such as water.

Certain of the inventive compounds, i.e., those where X is oxygen, are commonly denoted as "uracils" while other inventive compounds, i.e., those where X is hydrogen, are commonly denoted as "4(3H)-pyrimidinones". Although both types of compounds may be designated as substituted 1,3-diazin-4-ones, the more common nomenclature of "uracils" and "4(3H)-pyrimidinones" will be used in naming the compounds hereinafter.

The following are illustrative of the compounds of the invention:

3-methyl-5-bromo-6-(trifluoromethyl)uracil
3-propyl-5-bromo-6-(trifluoromethyl)uracil
3-nonyl-5-bromo-6-(trifluoromethyl)uracil
3-dodecyl-5-bromo-6-(trifluoromethyl)uracil
3-cyclopropyl-5-chloro-6-(trifluoromethyl)uracil
3-cyclohexyl-5-chloro-6-(trifluoromethyl)uracil
3-cyclobutyl-5-chloro-6-(trifluoromethyl)uracil
3-phenyl-5-methoxy-6-(trifluoromethyl)uracil
3-(2-carbomethoxypropyl)-5-fluoro-6-(trifluoromethyl)uracil
3-isopropyl-6-(trifluoromethyl)uracil
3-decyl-6-(trifluoromethyl)uracil
3-cyclopentyl-6-(trifluoromethyl)uracil
3-(2-butenyl)-6-(trifluoromethyl)uracil
3-allyl-6-(trifluoromethyl)uracil
3-phenyl-6-(trifluoromethyl)uracil
3-(4-chlorobutyl)-6-(trifluoromethyl)uracil
3-(1-ethylpropyl)-6-(trifluoromethyl)uracil
3-(3-bromo-2-methoxypropyl)-6-(trifluoromethyl)uracil
3-(m-trifluoromethylphenyl)-6-(trifluoromethyl)uracil
3-(2,4-dichlorophenyl)-6-(trifluoromethyl)uracil
3-(tolyl)-6-(trifluoromethyl)uracil
3-(2-carbomethoxypropyl)-6-(trifluoromethyl)uracil
3-methyl-5-chloro-6-trifluoromethyl-4(3H)-pyrimidinone
3-isopropyl-5-chloro-6-trifluoromethyl-4-(3H)-pyrimidinone
3-hexyl-5-chloro-6-trifluoromethyl-4(3H)-pyrimidinone
3-octyl-5-bromo-6-trifluoromethyl-4-(3H)-pyrimidinone
3-dodecyl-5-bromo-6-trifluoromethyl-4(3H)-pyrimidinone
3-cyclobutyl-5-bromo-6-trifluoromethyl-4(3H)-pyrimidinone
3-cyclohexyl-5-iodo-6-trifluoromethyl-4-(3H)- pyrimidinone
3-allyl-5-fluoro-6-trifluoromethyl-4(3H)-pyrimidinone
3-tolyl-5-t-butoxy-6-trifluoromethyl-4(3H)-pyrimidinone
3-(1-ethylpropyl)-5-bromo-6-trifluoromethyl-4(3H)-pyrimidinone
3-methyl-6-trifluoromethyl-4(3H)-pyrimidinone
3-propyl-6-trifluoromethyl-4-(3H)-pyrimidinone
3-isopropyl-6-trifluoromethyl-4(3H)-pyrimidinone
3-isobutyl-6-trifluoromethyl-4(3H)-pyrimidinone
3-hexyl-6-trifluoromethyl-4-(3H)-pyrimidinone
3-octyl-6-trifluoromethyl-4(3H)-pyrimidinone
3-undecyl-6-trifluoromethyl-4(3H)-pyrimidinone
3-cyclohexyl-6-trifluoromethyl-4(3H)-pyrimidinone
3-cyclopropyl-6-trifluoromethyl-4(3H)-pyrimidinone
3-allyl-6-trifluoromethyl-4(3H)-pyrimidinone
3-(2-butenyl)-6-trifluoromethyl-4(3H)-pyrimidinone
3-phenyl-6-trifluoromethyl-4(3H)-pyrimidinone
3-benzyl-6-trifluoromethyl-4(3H)-pyrimidinone
3-(2-methoxyethyl)-6-trifluoromethyl-4(3H)-pyrimidinone
3-(1-ethylpropyl)-6-trifluoromethyl-4(3H)-pyrimidinone
3-(2-bromopropyl)-6-trifluoromethyl-4(3H)-pyrimidinone
3-(2,3-dibromopropyl)-6-trifluoromethyl-4(3H)-pyrimidinone
3(2-carbomethoxypropyl)-6-trifluoromethyl-4(3H)-pyrimidinone
3-(3-bromo-2-methoxypropyl)-6-trifluoromethyl-4(3H)-pyrimidinone
3-tolyl-6-trifluoromethyl-4(3H)-pyrimidinone
3-(3,4-dichlorophenyl)-6-trifluoromethyl-4(3H)-pyrimidinone
3-(m-trifluoromethylphenyl)-6-trifluoromethyl-4-(3H)-pyrimidinone
3-(p-carboxyphenyl)-6-trifluoromethyl-4(3H)-pyrimidinone
3-(2-nitrophenyl)-6-trifluoromethyl-4(3H)-pyrimidinone
3-(p-aminophenyl)-6-trifluoromethyl-4(3H)-pyrimidinone The compounds for which a herbicidal usage is claimed may be similarly represented by formula (I) hereinabove with the provision that $R^2$ may be additionally hydrogen. It should be noted therefore that the herbicidal usage claims are of broader scope that the compound claims since certain compounds wherein $R^2$ is hydrogen are known, although the use of these compounds as herbicides is not known. Additional details in this regard are provided in the following portion of the specification.

THE PRIOR ART

The compounds 6-(trifluoromethyl)uracil and 5-nitro-6-(trifluoromethyl)uracil are disclosed in J. Org. Chem. 24, 113 (1959). 6-Trifluoromethyl-4(3H)-pyrimidinone is disclosed in J. Am. Chem. Soc. 80, 5750 (1958). In none of the above references is any utility stated for the compounds. These reference compounds and readily prepared derivatives thereof have therefore been specifically excluded from the compound claims appended hereto; however, the reference compounds are embraced within the herbicidal usage claims.

It should be noted that none of the reference compounds contain substitution in the number 3 ring position. It is known that direct and selective organic substitution of the number three nitrogen in a 1,3-diazine ring is usually unavailing since substitution will occur at other available ring positions to produce an undesirable product mixture. This route therefore could not be satisfactorily employed to produce selective organic substitution on the number 3 nitrogen as called for in the novel compounds of this invention.

The preferred method of selectively substituting a diazine ring with an organic substituent is to cyclize straight chain compounds which contain the desired organic substituent positioned on the proper atom prior to cyclization The reference compound, 6-(trifluoromethyl)uracil was prepared in this manner by condensing ethyl trifluoroacetoacetate with urea or thiourea respectively to produce the appropriate ring structures. It might appear that if substituted ureas containing organic substituents were used in this reaction in place of unsubstituted areas, uracils containing organic substitution on the number 3 nitrogen might be readily prepared. Surprisingly the reaction fails to proceed to any appreciable extent with such substituted ureas. Since the 5-nitro-6-(trifluoromethyl)uracil and the 6-trifluoromethyl-4-(3H)-pyrimidinone were simply prepared by treating 6-(trifluoromethyl)uracil by hitherto known techniques, it is the preparation of the basic uracil ring structure which is the important synthesis step. Therefore the first problem encountered in producing formula (I) compounds is the synthesis of a uracil ring containing the desired organic substituent in the number 3 nitrogen position.

U.S. Pat. No. 3,235,357 presents a process for preparing 6(alkyl)uracils containing organic substitution on the number 3-nitrogen. The two step process is shown in the following equations:

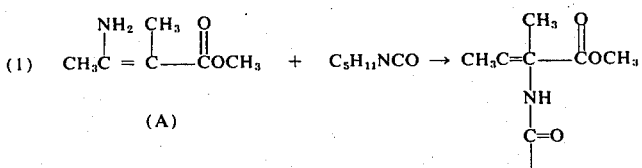

(A)      (B)

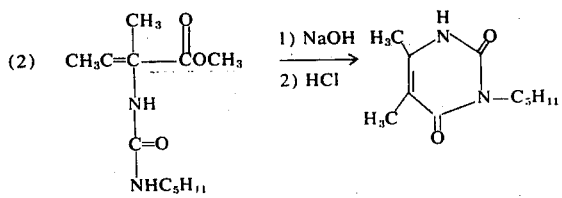

Step (1) occurs in a solvent such as benzene or toluene, followed by filtration to remove solids, and evaporation of the residue which removes the solvent from the filtrate to leave impure compound (B).

It might appear that this process would be readily adaptable to preparing similar 6-(trifluoromethyl)uracils by merely replacing the methyl group on the amino carbon in compound (A) with a trifluoromethyl group. However, when this was tried, reaction step (1) failed to proceed to any appreciable extent.

It becomes apparent that the simultaneous occurrence of organic sustituents on the number 3 nitrogen and the presence of a trifluoromethyl grouping in the formula (I) compound is a barrier to their preparation by related prior art processes. These barriers are conveniently overcome by practicing a novel single step process described hereinbelow.

U.S. Pat. No. 3,235,357 further discloses uracil structures which are useful herbicides. For example, certain of these compounds replace the trifluoromethyl group of Formula (I) compounds with chloro, bromo, chloroalkyl, and bromoalkyl. There are, however, several important aspects of these reference compounds which differ from the compounds of this invention. The reference compound does not refer to trifluoromethyl uracil since it is specifically limited to bromo and chloro derivatives. Furthermore, as the number 6 ring substituent is changed from monochloroalkyl to trichloroalkyl-substitution, herbicidal potency of the reference compounds diminishes. Such results conflict with the high herbicidal potency observed with the 6-trifluoromethyl-1,3-diazin-4-ones of this invention.

The reference compounds, while potent herbicides generally, do not exhibit a high degree of desirable selective herbicidal activity whereby useful vegetation such as farm crops is spared devastation while undesirable plants growing among the crops are destroyed. The compounds of the present invention on the other hand may be characterized as selective herbicides which demonstrate high potency toward the undesired plants growing among the crops while simultaneously failing to cause any substantial damage to useful crops, such as corn, cotton, sugar beets, soybeans, peanuts, and the like.

DESCRIPTION OF THE PREFERRED EMBODIMENTS

Certain of the invention compounds are conveniently prepared by a novel, single step process, this process being the subject of a copending application of A. W. Lutz, Ser. No. 737,288, filed concurrently herewith, now U.S. Pat. No. 3,580,913 dated May 25, 1971 and assigned to the present assignee.

In accordance with this process, 6-(trifluoromethyl)uracils of the formula:

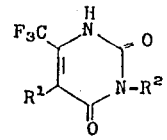

wherein $R^2$ is as previously defined, and $R^1$ is limited to hydrogen and water soluble salts of said compounds and tautomers thereof, are conveniently prepared by reacting an ester of a β-amino-α,β-unsaturated acid of the formula:

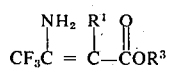

or tautomers thereof, with an isocyanate of the formula:

wherein $R^3$ is lower alkyl and $R^1$, $R^2$ are as defined immediately hereinabove, in the presence of a solvent and an alkali metal hydride or alkali metal lower alkoxide. The reaction proceeds in accordance with the following equation:

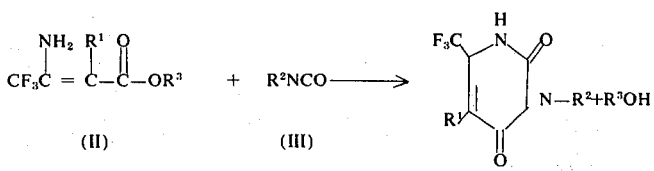

(II)     (III)

Reactant isocyanate (III) is readily prepared by a variety of hitherto known methods. The reactant acid ester (II) is likewise conveniently prepared by known techniques such as that of Jouille, in J. Org. Chem. 21, 1358 (1956).

It is an important aspect of this process that it be performed in the presence of an inert solvent and a solvent-soluble highly alkaline base to insure the satisfactory progression of the reaction.

Among the solvents which are suitable are aromatic solvents containing from 6 to 8 carbon atoms such as toluene, benzene, xylene; lower alkanols containing from 1 to 8 carbon atoms such as methanol, ethanol, isopropanol, butanol, pentanol, octanol, t-butanol; low molecular weight (i.e., a molecular weight not exceeding about 200) glycol ethers such as diethylene glycol dimethyl ether (diglyme), ethylene glycol dimethyl ether (glyme), diethylene glycol diethyl ether, and ethylene glycol diethyl ether; and dipolar aprotic solvents, i.e., solvents which are substantially chemically inert toward reactants (II) and (III) as well as product (I), which have a coordinated valence link between two originally neutral atoms whereby one loses and the other gains a share of two electrons, and which neither yields a proton to the solute, nor gains one from it. Illustrative dipolar aprotic solvents are dimethylsulfoxide (a highly preferred solvent), dimethylformamide, acetone, methyl isobutyl ketone, acetonitrile, nitrobenzene, N,N-dimethylacetamide, and the tetrahydrosulfolanes such as tetrahydrothiophene dioxide.

embraced within formula (I), the corresponding uracil may be prepared as described above. Then using well known methods, the oxygen on the number 2 ring position can be removed to leave the desired 4(3H)-pyrimidinone.

The following examples are provided to further illustrate the invention.

EXAMPLE 1

Preparation of 3-isopropyl-6-(trifluoromethyl)uracils

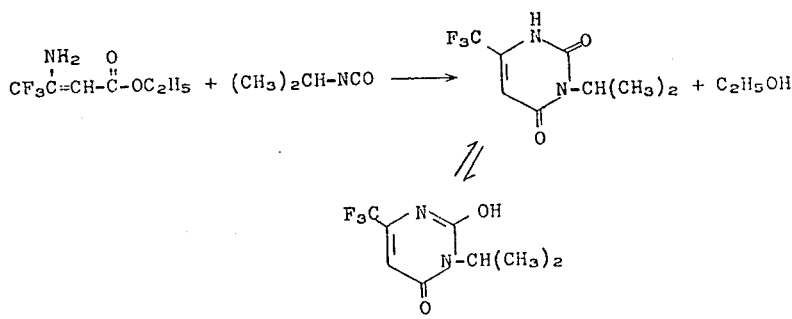

Suitable bases are potassium tertiary butoxide (the preferred base), sodium methoxide, sodium propoxide, sodium hydride, potassium hydride, and lithium hydride. A preferred amount of base is about 0.9 to about 1.1 moles per mole of reactant.

A highly preferred solvent-base system is that of dimethylsulfoxide and potassium tertiary butoxide because of the increased product yields observed therewith. The solvent-base system, however, is not limited to a single solvent and base and may include combinations such as a single base with more than one solvent, a single solvent with more than one base, or simultaneously more than one solvent and more than one base.

The process appears insensitive to pressure and may be carried out at atmospheric, sub-atmospheric or superatmospheric pressures. Temperatures between about 15°C. and about 100°C. are suitable. Preferred conditions are atmospheric pressure and a temperature range of about 25°C. to about 50°C.

The products (I) prepared by this process may be readily converted into their corresponding acid or base salts by reaction with the appropriate acid or base employing known methods.

When the substituents are halo in the number 5 ring position, recommended procedure is to prepare the desired ring structure in accordance with the above process but leaving the number 5 ring position unsubstituted. This position can be subsequently substituted using conventional methods of direct halogenation, such as shown by way of illustration in Examples 19-31 hereinbelow.

When it is desired to prepare 4(3H)-pyrimidinones

A solution of ethyl 3-amino-4,4,4-trifluorocrotonate (10.7 g., 0.058 mole) in 20 ml. of anhydrous dimethyl sulfoxide was added in portions with stirring to a solution of potassium tert-butoxide (8.55 g., 0.058 mole) in 50 ml. dimethyl sulfoxide. Cooling was required to maintain the temperature at 25°C.

Isopropylisocyanate (5.48 g., 0.64 mole) was added all at once with vigourous stirring to the above solution. After one hour the yellow solution was poured into a large volume of water and this solution extracted three times with ether. The ether layers were discarded. The aqueous phase was acidified to pH 1 with hydrochloric acid and then extracted three times with ether. After washing the ether extract with water, drying and stripping in vacuo, a pale yellow solid residue of 11.3 g. (87.0%) remained. The product was recrystallized from water to give the analytical sample which had a melting point of 139°–142°C.

$C_8H_9F_3N_2O_2$ requires: C, 43.25; H, 4.08; F, 25.65; N, 12.61. found: C, 43.24; H, 3.93; F, 25.45; N, 12.72.

EXAMPLES 2–15

Following substantially the same procedure as that of Example 1, except for variations in the reactant isocyanate used, the compounds presented in Table I were prepared.

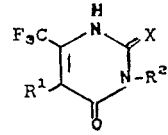

TABLE I

| Example No. | Reactant Isocyanate | X | $R^1$ | $R^2$ | Melting Point (°C.) |
|---|---|---|---|---|---|
| 2 | methyl | OH | H | $CH_3$ | 237–238.5 |
| 3 | ethyl | OH | H | $C_2H_5$ | 199–200.5 |
| 4 | n-propyl | OH | H | $n-C_3H_7$ | 173–174 |
| 5 | n-butyl | OH | H | $n-C_4H_9$ | 174–176 |
| 6 | sec-butyl | OH | H | $sec-C_4H_9$ | 106.5–108 |
| 7 | t-butyl | OH | H | $t-C_4H_9$ | 165–167 |
| 8 | n-octyl | OH | H | $n-C_8H_{17}$ | 130–133.5 |
| 9 | n-dodecyl | OH | H | $n-C_{12}H_{25}$ | 121–123 |

TABLE I-continued

| Example No. | Reactant Isocyanate | X | R¹ | R² | Melting Point (°C.) |
|---|---|---|---|---|---|
| 10 | cyclohexyl | OH | H | cyclohexyl | 195–197 |
| 11 | phenyl | OH | H | phenyl | 235–236.5 |
| 12 | 3,4-dichlorophenyl | OH | H | 3,4-dichlorophenyl | 238–239 |
| 13 | carbethoxymethylene | OH | H | $CH_2COC_2H_5$ | 149–150.5 |
| 14 | allyl | OH | H | $CH_2CH=CH_2$ | 158–160 |
| 15 | 4-fluorophenyl | OH | H | 4-fluorophenyl | 188–189 |
| 16 | 2-fluorophenyl | OH | H | 2-fluorophenyl | 200–202 |
| 17 | 3-fluorophenyl | OH | H | 3-fluorophenyl | 244–245 |
| 18 | 3-trifluoromethylphenyl | OH | H | 3-trifluoromethylphenyl | 174–175 |

EXAMPLE 19

Preparation of 3-isopropyl-5-bromo-6-(trifluoromethyl)uracil

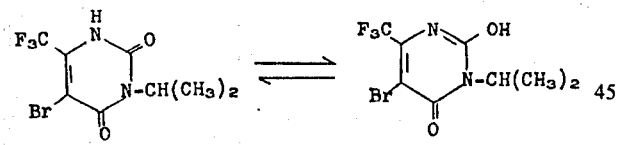

3-isopropyl-6-(trifluoromethyl)uracil as prepared in Example 1 (7.4 g., 0.033 mole) was dissolved in a mixture of 0.5N NaOH (0.04 mole) and chloroform (15 ml.). A solution of bromine (5.89 g., .036 mole) in 25 ml. chloroform was added in portions with stirring. After the addition was complete, the reaction mixture was stirred for one-half hour before discharging the bromine color with sodium bisulfite. The layers were separated, and the aqueous layer extracted with fresh chloroform. The combined chloroform extracts were washed with water and then evaporated to dryness leaving 10.1 g. (100%) of white solid residue. One recrystallization from benzene gave a product with a melting point of 146°–150°C. The analytical sample melted at 149°–150°C.

$C_8H_8BrF_3N_2O_2$ requires: C, 31.92; H, 2.67; Br, 26.54; F, 18.93; N, 9.30. found: C, 31.94; H, 2.68; Br, 26.56; F, 19.18; N, 9.22.

EXAMPLES 20–31

Following substantially the same procedure as that of Example 19, 5-bromo derivatives of the compounds prepared in Examples 2 to 13 were prepared. Melting points are presented in Table II.

TABLE II

| Example No. | 5-Bromo Derivative of Compound Prepared In: | Melting Point (°C.) |
|---|---|---|
| 20 | Example 2 | 212–213.5 |
| 21 | Example 3 | 197–198 |
| 22 | Example 4 | 169–172 |
| 23 | Example 5 | 128.5–130 |
| 24 | Example 6 | 130–132 |
| 25 | Example 8 | 98–101.5 |
| 26 | Example 9 | 101–102 |
| 27 | Example 10 | 187–189 |
| 28 | Example 11 | 207–209 |
| 29 | Example 12 | 239–240.5 |
| 30 | Example 13 | 185–188 |

(31.) The 5-bromo derivative of 3-(2,3-dibromopropyl)-6-(trifluoromethyl)uracil was similarly prepared, melting point: 154°–155.5°C.

EXAMPLE 32

Preparation of 5-bromo-6-(trifluoromethyl)uracil

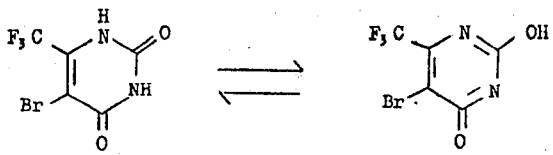

6-(Trifluoromethyl)uracil (4.0 g., 0.22 mole) was dissolved in 75 ml. water at 70°C. Bromine (3.55 g., 0.022 mole) was added in portions with vigorous stirring. A white precipitate formed almost immediately. The suspension was allowed to cool to room temperature and then chilled before being filtered. The product after air drying weighed 4.75 g. (82.5%) and had a melting point of 231°–234°C. The analytical sample melting point was 236°–240°C. After recrystallization from water.

$C_5H_2Br_2F_3N_2O_2$ requires: C, 23.19; H, 0.78; N, 10.82; Br, 30.86. found: C, 23.04; H, 0.89; N, 11.05; Br, 30.85.

EXAMPLE 33

Preparation of 5-chloro-3-n-butyl-6-(trifluoromethyl)uracil

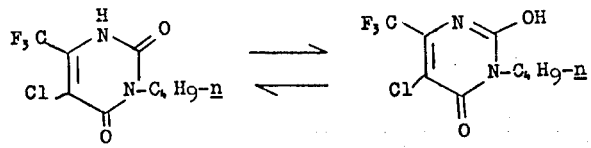

3-n-butyl-6-(trifluoromethyl)uracil (1.0 g.) was dissolved in 15 ml. of 5.25% sodium hypochlorite solution and allowed to stand at room temperature for 1 hour. The suspension which was present was acidified to pH 1 with hydrochloric acid and the solid removed by filtration. After purification by chromatography and recrystallization from cyclohexane, the product had a melting point of 138°–139°C.

$C_9H_{10}ClF_3N_2O_2$ requires; C, 39.94; H, 3.72; Cl, 13.10; F, 21.06; N, 10.35. found: C, 39.72; H, 3.81; Cl, 12.99; F, 20.92; N, 10.24.

EXAMPLES 34 to 35

Following substantially the same procedure as that of Example 33, the following compounds were prepared:

| Example No. | Compound | Melting Point (°C.) |
|---|---|---|
| 34 | F₃C, Cl, N-CH(CH₃)₂ structure | 138–141 |
| 35 | F₃C, Cl, N-CH₃, CH(C₂H₅) structure | 103–106 |

UTILITY

The invention compounds as well as formula (I) compounds wherein $R^2$ may be additionally hydrogen are effective preemergence and postemergence herbicides useful for the control of monocotyledonous and dicotyledonous plants as amply shown by the date of Examples 36 and 37 hereinbelow.

Application of the compounds of the invention for purposes of herbicidal control can be accomplished employing both conventional type formulations and equipment. The compounds may, for instance, be formulated as wettable powders, dusts, dust concentrates, emulsifiable concentrates and the like which are amenable to application with conventional spraying or dusting apparatus.

Wettable powder formulations are generally prepared by admixing from about 25% to about 95%, by weight, of active ingredients with finely ground clay, such as kaolin or attapulgite, either with or without a surface active agent, emulsifier or spreader-sticker. The latter is then dispersed in water for spray application.

Dusts and dust concentrates are similarly prepared using from about 5% to about 95% of active ingredient and from about 95% to about 5% of finely divided inert ingredients. These dusts are generally applied as such, or they may be further diluted with finely ground inert solids and then applied with conventional dusting apparatus.

Emulsifiable concentrates may be prepared by dissolving or dispersing the active ingredient in organic solvent, with or without emulsifying agents, surfactants or the like. Such formulations are then diluted with either water or an appropriate organic diluent prior to application.

The following additional examples are provided to illustrate the herbicidal activity of the compounds.

EXAMPLE 36

Pre-Emergence Herbicidal Activity of Substituted-6-Trifluoromethyl-1,3-Diazin-4-ones The preemergent herbicidal activity of the compounds is exemplified by the following tests in which the seeds of a variety of monocotyledonous and dicotyledonous plants are separately mixed with potting soil and the mixture placed on top of several inches of potting soil in separate pint cups. After planting, the cups are sprayed with the selected aqueous-acetone solution containing the test compound in sufficient quantity to provide the desired equivalent of four pounds per acre of test compound per cup. The treated cups are then placed on greenhouse benches and cared for in the usual manner, in accordance with greenhouse procedures. Three weeks after treatment, the tests are terminated and each cup is examined and rated according to the defined Herbitoxicity Index given in the table below. The tabulated results of these tests presented in Table III establish the herbicidal proficiency of the test compounds.

Herbitoxicity Index

9 = 100% reduction in stand
9—= 1 or 2 stunted plants remaining
8 = 85– <100% reduction in stand
7 = 70– <85% reduction in stand
6 = 60– <70% reduction in stand 5 = 50– <60% reduction in stand
4 = 40– <50% reduction in stand
3 = 30– <40% reduction in stand
2 = 20– <30% reduction in stand
1 = 10– <20% reduction in stand
0 = no apparent effect
a = abnormal, malformed, twisted
c = chlorotic
g = unusual physiological effect
m = moderate injury
r = regrowth
s = severe injury
t = trace to slight injury
— = no test Abbreviations for the plant species employed in the herbicidal activity tests of Examples 36 and 37 are as follows:

| | | | |
|---|---|---|---|
| Rag = Ragweed | | Cor = Corn | |
| Ko = Kochia | | Cot = Cotton | |
| La = Lambsquarters | | Soy = Soybeans | |
| Mu = Mustard | | SB = Sugar Beets | |
| Pi = Pigweed | | AW = Alligator Weed | |
| Ba = Barnyard grass | | BW = Bindweed | |
| Cr = Crabgrass | | CT = Canada Thistle | |
| GF = Green Foxtail | | JG = Johnson Grass | |
| WO = Wild Oats | | NS = Nutsedge | |
| | | QG = Quackgrass | |

Compounds identified by ++ were rated according to the following rating system:

| Rating System | % Difference in Growth from the Check[1] |
|---|---|
| 0 - no effect | 0 |
| 1 - possible effect | 1–10 |
| 2 - slight effect | 11–25 |
| 3 - moderate effect | 26–40 |
| 5 - definite injury | 41–60 |
| 6 - herbicidal effect | 61–75 |
| 7 - good herbicidal effect | 76–90 |
| 8 - approaching complete kill | 91–99 |
| 9 - complete kill | 100 |
| 4 - abnormal growth, i.e., a definite physiological malbut with an over-all effect less than a 5 on the rating scale | |

[1]Based on visual determination of stand, size, vigor, chlorosis, growth malformation and over-all plant appearance.

TABLE III

PRE-EMERGENCE HERBICIDAL DATA AT A DOSAGE OF 4 LBS./ACRE

| X | R$^1$ | R$^2$ | Rag | Ko | La | Mu | Pi | Ba | Cr | GF | WO | Cor | Cot | Soy | SB |
|---|---|---|---|---|---|---|---|---|---|---|---|---|---|---|---|
| OH | H | CH$_3$ | 3 | — | 9⁻ | 9⁻ | 9 | 9⁻ | 9⁻ | mg | 9c | mg | 0 | m | 0 |
| OH | H | C$_2$H$_5$ | 9 | — | 9 | 9 | 9 | 9⁻ | 9⁻ | 9 | 9 | 0 | 9 | 8 | 9 |
| OH | H | n-C$_3$H$_7$ | 9 | — | 9 | 9 | 9 | 9 | 9 | 9⁻ | 9⁻ | tg | 9 | m | 9 |
| OH | H | i-C$_3$H$_7$ | — | 9 | 9 | 9 | 9 | 9 | 9 | 9 | 9 | mg | 9 | 8 | 9 |
| OH | H | n-C$_4$H$_9$ | — | 9 | 9⁻ | 9 | 8 | 8 | 8g | 8g | t | 0 | m | 0 | 9 |
| OH | H | sec-C$_4$H$_9$ | — | 9 | 9 | 9 | 9 | 9⁻ | 9 | 9 | 9 | sg | 9 | 9 | 9 |
| OH | H | n-C$_8$H$_{17}$ | — | 0 | 5g | 9c | 3g | mg | mg | 3g | 8 | 0 | 0 | tc | 0 |
| OH | H | n-C$_{12}$H$_{25}$ | 0 | — | 9 | 9 | 0 | 3g | mg | 9 | s | tg | 0 | t | tg |
| OH | H |  | — | 9⁻ | 9⁻ | 9 | 7g | 7g | 4g | tg | 0 | 0 | 9⁻ | mc | 8 |
| OH | H |  | 9 | — | 9 | 9 | 9 | 3g | 8g | mg | 9 | mg | 9 | 9 | 9 |
| OH | H | 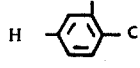 | 9 | — | 9 | 9 | 9⁻ | 3g | 9 | 8g | 0 | tg | t | 9 | 7 |
| OH | H | CH$_2$ĊOC$_2$H$_5$ | — | tg | 5 | 9⁻ | 0 | 5 | 9 | 9 | 0 | 0 | 0 | 0 | 9 |
| OH | Br | H | — | 9 | 9 | 9 | 9 | 9⁻ | 9 | 5 | 9⁻ | 9 | 9 | 9 | 9 |
| OH | Br | CH$_3$ | 3 | — | 5g | 9 | 9 | 7g | 9 | 3g | tg | — | — | — | — |
| OH | Br | C$_2$H$_5$ | — | 9 | 9 | 9 | 9 | 9 | 9 | 9⁻ | 9 | 9 | 9 | 9 | 9 |
| OH | Br | n-C$_3$H$_7$ | — | 9 | 9 | 9 | 9 | 9 | 9 | 9 | 9 | 9 | 5 | 3 | 9 |
| OH | Br | i-C$_3$H$_7$ | — | 9 | 9 | 9 | 9 | 9 | 9 | 9⁻ | tg | 7 | 7 | 9 |
| OH | Br | n-C$_4$H$_9$ | — | 9⁻ | 9⁻ | 9⁻ | 3 | tg | tg | 0 | 0 | 0 | t | 0 | 3 |
| OH | Br | sec-C$_4$H$_9$ | — | 9 | 9 | 9 | 9 | 9c | 9c | 9 | 9c | 9 | s | tg | 9 |
| OH | Br | n-C$_8$H$_{17}$ | — | 0 | 0 | 0 | tg | 3g | 0 | 0 | 0 | 0 | t | 0 | 0 |
| OH | Br | n-C$_{12}$H$_{25}$ | — | 0 | 9⁻ | 9 | 9⁻ | 0 | 9 | 0 | 0 | mg | 0 | 9 | 7 |
| OH | Br |  | — | 9⁻ | 9⁻ | 9 | 3g | tg | 3g | 0 | 0 | 0 | 0 | 0 | 3 |
| OH | Br |  | 9 | — | 9 | 9 | 9 | mg | 3g | mg | 9 | mg | 9 | 9 | 9 |
| OH | Br |  | — | tg | mg | 9⁻ | 9 | 0 | mg | tg | 0 | 0 | 0 | 0 | 5 |
| OH | Br | CH$_2$ĊOC$_2$H$_5$ | — | 5 | 9 | tg | 9⁻ | 5 | 9 | 9 | 0 | 0 | 0 | 0 | 7 |
| OH | Cl | i-C$_3$H$_7$ | — | 9 | 9 | 9 | 9 | 9 | 9 | 9 | 9 | 4g | 9 | 9a | 9 |
| OH | Cl | n-C$_4$H$_9$ | 8 | — | 9 | 9 | 5g | tg | 4g | 3g | ta | — | — | — | — |
| OH | Cl | sec-C$_4$H$_9$ | — | 9 | 9 | 9 | 9 | 9⁻ | 9 | 9 | 8 | m | 9 | mg | 9 |

TABLE III-continued

| | | | PRE-EMERGENCE HERBICIDAL DATA AT A DOSAGE OF 4 LBS./ACRE | | | | | | | | | | | | |
|---|---|---|---|---|---|---|---|---|---|---|---|---|---|---|---|
| X | R¹ | R² | Rag | Ko | La | Mu | Pi | Ba | Cr | GF | WO | Cor | Cot | Soy | SB |
| OH | H | H | — | 9 | 9⁻ | 9 | 9⁻ | 8g | 8g | 8g | 9 | t | 8s | sc | 9 |
| H | H | H | — | 9 | 9 | 9 | 9⁻ | 0 | 5 | mg | 9 | 0 | 3s | 9 | 9 |
| OH | H | CH₂CH=CH₂ | — | 9 | 9 | 9 | 9 | 7g | 9 | 9 | 9 | tg | 9 | mg | 9 |
| ⁺⁺OH | H |  | 9 | — | 9 | 9 | 9 | 9 | 9 | 9 | 9 | 8 | 9 | 8 | 9 |
| ⁺⁺OH | H |  | 8 | — | 9 | 9 | 8 | 8 | 6 | 2 | 9 | 5 | 9 | 8 | 9 |
| ⁺⁺OH | H |  | 9 | — | 9 | 9 | 9 | 9 | 8 | 5 | 9 | 7 | 9 | 8 | 9 |
| ⁺⁺OH | H |  | 9 | — | 9 | 9 | 9 | 8 | 9 | 9 | 9 | 6 | 9 | 8 | — |

EXAMPLE 37

Post-Emergence Herbicidal Activity of Substituted-6-Trifluoromethyl-1,3-Diazin-4-ones The postemergence herbicidal activity of the compounds is demonstrated by treating a variety of monocotyledonous and dicotyledonous plants with the compounds dispersed in aqueous-acetone mixtures. In the test seedling plants are grown in jiffy flats for about 2 weeks. The test compounds are dispersed in 50/50 acetone/water mixtures insufficient quantity to produce the desired concentrations of about 4 pounds per acre of active compound when applied to the plants through a spray nozzle operating at 30 psi for a predetermined time. After spraying, the plants are placed on greenhouse benches and are cared for in the usual manner, commensurate with conventional greenhouse practices. Two weeks after treatment, the seedling plants are examined and rated in Table IV below according to the Herbitoxicity Index provided in Example 36.

TABLE IV

| | | | POST EMERGENCE HERBICIDAL DATA AT A DOSAGE OF 4 LBS./ACRE | | | | | | | | | | | | | | |
|---|---|---|---|---|---|---|---|---|---|---|---|---|---|---|---|---|---|
| X | R¹ | R² | AW | BW | CT | JG | NS | QG | Rag | Ko | La | Mu | Pi | Ba | Cr | GF | WO |
| OH | H | CH₃ | mc | t | m | 0 | 0 | 0 | — | 9 | 9 | 9 | 9 | 9 | 9 | 9 | 9 |
| OH | H | C₂H₅ | tc | 9 | 9 | 0 | 0 | s | — | 9 | 9 | 9 | 9 | 9 | 9 | 9 | 9 |
| OH | H | n-C₃H₇ | tc | 9 | 9 | t | t | 9 | — | 9 | 9 | 9 | 9 | 9 | 9 | 9 | 9 |
| OH | H | i-C₃H₇ | m | 9 | 9 | t | t | m | — | 9 | 9 | 9 | 9 | 9 | 9 | 9 | 9 |
| OH | H | n-C₄H₉ | 0 | 9 | 9 | 0 | 0 | s | — | 9 | 9 | 9 | 5m | 9 | 9 | 9 | 9 |
| OH | H | sec-C₄H₉ | t | 9 | 9 | 9r | 0 | t | 9 | — | 9 | 9 | 9 | 9 | 9 | 9 | 9 |
| OH | H | n-C₈H₁₇ | 0 | t | 0 | 0 | 0 | 0 | — | 9 | mg | mg | mg | t | t | t | 0 |
| OH | H | n-C₁₂H₂₅ | 0 | 0 | 0 | 0 | 0 | 0 | — | 0 | ta | tc | t | 0 | 0 | 0 | 0 |
| OH | H |  | 0 | 9r | 9 | 0 | 0 | 0 | — | 9 | 9 | 9 | 9 | 7 | 8 | 9 | t |
| OH | H |  | tc | 9 | 9 | t | 0 | t | — | 9 | 9 | 9 | 9 | 9 | 9 | 9 | 9 |
| OH | H |  | 0 | 9 | 9 | t | 0 | t | — | 9 | 9 | 9 | m | 9⁻ | 8 | 9 | 3 |
| ⁺⁺OH | H |  | — | — | — | — | — | — | 9 | —9 | 9 | 9 | 9 | 9 | 9 | 9 | |
| ⁺⁺OH | H |  | — | — | — | — | — | — | 9 | — | 9 | 9 | 9 | 9 | 9 | 9 | 9 |
| OH | H | CH₂ĊOC₂H₅ | | 9 | 9 | 0 | 0 | 0 | 9 | — | 9⁻ | 9 | t | 9⁻ | 9 | 9 | t |
| OH | Br | H | — | — | — | — | — | — | — | 9 | 9 | 9 | 9 | 5 | 9⁻ | 5 | 9 |
| OH | Br | CH₃ | — | — | — | — | — | — | 9 | — | 9 | 9 | 9 | 9 | 9 | 8 | 9 |
| OH | Br | C₂H₅ | m | 9 | 9 | m | t | m | 9 | — | 9 | 9 | 9 | 9 | 9 | 9 | 9 |
| OH | Br | n-C₃H₇ | t | 9 | 9 | t | t | m | 9 | — | 9 | 9 | 9 | 9 | 9⁻ | 9 | 9⁻ |
| OH | Br | i-C₃H₇ | 9 | 9 | 9 | 9⁻ | t | s | — | 9 | 9 | 9 | 9 | 9 | 9⁻ | 9 | 9 |
| OH | Br | n-C₄H₉ | t | 9 | 9 | t | t | t | 9 | — | 9 | 9 | 9 | 9 | 9⁻ | 9 | 9 |
| OH | Br | sec-C₄H₉ | 9 | 9 | 9 | 9 | mr | 9 | 9 | — | 9 | 9 | 9 | 9 | t | — | t | 5 |
| OH | Br | n-C₈H₁₇ | t | 9 | 9 | 0 | 0 | 0 | 9 | — | 9 | 9 | 9 | t | 9 | t | 5 |
| OH | Br | n-C₁₂H₂₅ | 0 | 9r | t | 0 | 0 | 0 | 5 | — | s | s | m | 3 | t | t | t |
| OH | Br |  | 0 | 9 | 9 | 0 | 0 | 0 | — | 9 | 9 | 9 | 9 | 7 | 7 | 5 | t |

TABLE IV-continued

| X | R¹ | R² | POST EMERGENCE HERBICIDAL DATA AT A DOSAGE OF 4 LBS./ACRE | | | | | | | | | | | | | | |
|---|---|---|---|---|---|---|---|---|---|---|---|---|---|---|---|---|---|
| | | | AW | BW | CT | JG | NS | QG | Rag | Ko | La | Mu | Pi | Ba | Cr | GF | WO |
| OH | Br | (phenyl-Cl) | tc | 9 | 9 | 0 | 0 | t | — | 9 | 9 | 9 | 9 | 9⁻ | 9 | 9 | 9⁻ |
| OH | Br | (phenyl-Cl,Cl) | t | 9 | 9 | 0 | 0 | 0 | 9 | — | s | 9 | 9 | 5 | 5 | 9 | t |
| OH | Br | $CH_2COC_2H_5$ | 0 | 9 | 9 | 0 | 0 | 0 | 9 | — | 9⁻ | 9 | t | 9 | 9 | 9 | t |
| OH | Br | $CH_2CHCH_2$ (Br Br) | — | — | — | — | — | — | — | 8 | 9 | 9 | 5 | m | 9⁻ | 9⁻ | 3m |
| OH | H | H | — | — | — | — | — | — | — | 9⁻ | 9 | 9 | 9⁻ | tg | tg | tg | 9 |
| OH | H | $CH_2CH=CH_2$ | tc | 9 | 9 | t | 0 | 0 | — | 9 | 9 | 9 | 9 | 9 | 9⁻ | 9 | 9 |
| OH | Cl | $i-C_3H_7$ | gc | 9 | 9 | mr | t | t | 9 | 9 | 9 | 9 | 9 | 7 | 9⁻ | 9 | 9⁻ |
| OH | Cl | $n-C_3H_9$ | — | — | — | — | — | — | — | 9 | 9 | 9 | 9 | 8 | 9 | 9 | 7 |
| OH | Cl | $sec-C_4H_9$ | src | 9r | 9 | t | 5 | t | — | 9 | 9 | 9 | 9 | 9 | 9 | — | — |
| ⁺⁺OH | H | (phenyl-F) | — | — | — | — | — | — | 9 | — | 9 | 9 | 9 | 9 | 9 | 9 | 9 |
| ⁺⁺OH | H | (phenyl-F) | — | — | — | — | — | — | 9 | — | 9 | 9 | 9 | 9 | 9 | 9 | 9 |

We claim:

1. A method for controlling undesirable plant species which comprises applying to soil containing the undesirable plant species a herbicidally effective amount of a compound of the formula:

$$\begin{array}{c} F_3C \diagdown \diagup N \diagdown X \\ R_1 \diagdown \diagup N-R_2 \\ O \end{array}$$

wherein
R₁ is hydrogen or halo,
R₂ is alkyl of 1 to 12 carbon atoms, cyclohexyl, phenyl, allyl, hydrogen or mono or dihalo substituted alkyl of 1 to 12 carbon atoms, monocarb (loweralkoxy) substituted alkyl of 1 to 12 carbon atoms, mono or dihalo substituted phenyl, or mono or di CF₃ substituted phenyl, and X is hydrogen or hydroxy and where X is hydroxy, the tautomers and water soluble sodium, potassium, ammonium and tri(C₁-C₄ alkyl) ammonium salts.

2. A method according to claim 1 wherein X of the formula is hydroxy, R₁ is hydrogen and R₂ is alkyl having from 1 to 12 carbon atoms.

3. A method according to claim 1 wherein X of the formula is hydroxy, R₁ is chloro or bromo and R₂ is alkyl having from 1 to 12 carbon atoms.

4. A method according to claim 1 wherein the compound is 3-isopropyl-6-(trifluoromethyl)uracil.

5. A method according to claim 1 wherein the compound is 3-isopropyl-5bromo-6-(trifluoromethyl)uracil.

6. A method according to claim 1 wherein the compound is 3-isopropyl-5-chloro-6-(trifluoromethyl)uracil.

7. A method according to claim 1 wherein X of the compound is hydroxy, R₁ is hydrogen, R₂ is p-fluorophenyl or m-trifluoromethylphenyl.

8. A method according to claim 1 wherein the compound is 3-s-butyl-5-bromo-6-(trifluoromethyl)uracil.

* * * * *